United States Patent [19]

Galliani et al.

[11] Patent Number: 5,015,655

[45] Date of Patent: May 14, 1991

[54] 1-AZABICYCLOALKANE DERIVATIVES, THEIR PREPARATION PROCESS AND THEIR USE AS MEDICAMENTS

[75] Inventors: Giulio Galliani; Fernando Barzaghi, both of Monza; Carla Bonetti, Fontanella; Emilio Toja, Milan, all of Italy

[73] Assignee: Roussel UCLAF, Paris, France

[21] Appl. No.: 426,778

[22] Filed: Oct. 26, 1989

[30] Foreign Application Priority Data

Oct. 28, 1988 [IT] Italy .............................. 22452 A/88

[51] Int. Cl.$^5$ ...................... A61K 31/40; C07D 209/02
[52] U.S. Cl. ..................................... 514/413; 548/452
[58] Field of Search .......................... 548/452; 514/413

[56] References Cited

PUBLICATIONS

Zhur Obshchei Khim 27, 72 (1957), pp. 77–83.
Helv. Chim. Acta, 46, 1963, No. 299, 2658-2666 Von C. A. Grob & J. Zergenyi, "3–Substituierte Dehydrochinuclidine ... ".
Helv. Chim. Acta, 55, 1972, No. 243, 2439-2447 Von C. A. Grob, W, Simon & W. D. Treffert, "Die Syntheses Von 4–Akylchin ... ".
Heterocycles, vol. 24, No. 4, 1986, pp. 971–977 Ricciardi et al, "Facile Synthesis of Styrylquinuclidines".
Helv. Chim. Acta, 57, 1974, No. 253, 2332-2338 Von Eros Ceppi & Cyril A. Grob, "Synthese und Basizitata 4–Substituierter ... ".
Chemical Abstracts Service: Abstracts Numbers: (Registry numbers of Compds): RN 126453-45-0, 126343-69-9, 126343-66-6, 126343-90-6, 126343-64-4, 126453-42-7, 126343-68-8, 126453-43-8, 126343-67-7, 126453-44-9, 126343-72-4.

Primary Examiner—Frederick E. Waddell
Assistant Examiner—Catherine S. Scalzo
Attorney, Agent, or Firm—Stevens, Davis, Miller & Mosher; Stevens, Davis, Miller & Mosher

[57] ABSTRACT

Compounds useful in the treatment of Alzheimers's disease, senile dementia or memory disorders of the aged of the formula

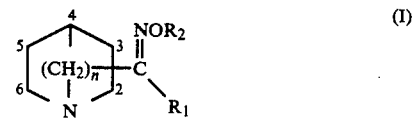

in which
n represents the number 1, 2 or 3,
$R_1$ and $R_2$, identical or different, represent hydrogen, a linear, branched or cyclic alkyl, alkenyl, or alkynyl which contain up to 6 carbon atoms, $R_1$ and $R_2$ optionally substituted by hydroxy, alkoxy containing up to 6 carbon atoms, aralkyl containing up to 14 carbon atoms, a COOalk$_1$ radical in which alk$_1$ represents alkyl containing up to 6 carbon atoms, a —CON(alk$_2$)$_2$ radical in which alk$_2$ represents alkyl containing up to 6 carbon the radical —C($R_1$)=NOR$_2$ being in position 2, 3 or 4, in all their isomer forms and their mixture, as well as their addition salts with pharmaceutically acceptable organic or mineral acids. Also therapeutic compositions containing the compounds, method of treatment and method of preparation.

20 Claims, No Drawings

1-AZABICYCLOALKANE DERIVATIVES, THEIR PREPARATION PROCESS AND THEIR USE AS MEDICAMENTS

The present invention relates to new 1-azabicycloalkane derivatives, their preparation process and their use as medicaments.

A subject of the invention is the compounds of general formula (I):

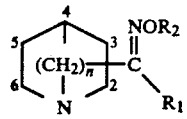

in which
n represents the number 1, 2, or 3,
$R_1$ and $R_2$, identical or different, represent hydrogen, a linear, branched or cyclic alkyl, alkenyl, or alkynyl which contains up to 6 carbon atoms, $R_1$ and $R_2$ being optionally substituted by hydroxy, alkoxy containing up to 6 carbon atoms, aralkyl containing up to 14 carbon atoms, a COOalk$_1$ radical in which alk$_1$ represents alkyl containing up to 6 carbon atoms, a —CON(alk$_2$)$_2$ radical in which alk$_2$ represents alkyl containing up to 6 carbon atoms, the radical —C(R$_1$)=NOR$_2$ being in position 2, 3 or 4, in all their isomer forms and their mixtures, as well as their addition salts with pharmaceutically acceptable organic or mineral acids.

Among the addition salts with acids, there can be mentioned those formed with mineral acids, such as hydrochloric, hydrobromic, sulfuric or phosphoric, or with organic acids such as formic, acetic, propionic, benzoic, maleic, fumaric, succinic, tartaric, citric, oxalic, glyoxylic, aspartic, alkanesulphonic such as methane- or ethanesulphonic, arenesulphonic such as benzene- or para-toluenesulphonic.

When $R_1$ or $R_2$ represents a linear or branched alkyl, it is preferred to be methyl, ethyl, n-propyl, isopropyl, n-butyl, secbutyl, isobutyl, n-pentyl, n-hexyl, tert-butyl, tert-pentyl, neopentyl or n-hexyl.

When $R_1$ or $R_2$ represents cyclic alkyl, it is preferred to be cyclopropyl, cyclobutyl, cyclopentyl, cyclohexyl, cyclopropylmethyl, cyclobutylmethyl, cyclopentylmethyl, or cycloheyxylmethyl.

When $R_1$ or $R_2$ represents alkenyl or alkynyl, it is preferred to be an ethylene radical such as, for example, vinyl, allyl, 1,1,-dimethylallyl or 2-butenyl, or an acetylene radical such as, for example, ethynyl or propynyl.

By alkoxy is preferred linear or branched methoxy, ethoxy, propoxy or butoxy.

The aralkyl is preferably benzyl or phenethyl.

The radicals alk$_1$ and alk$_2$ preferably represent methyl or ethyl.

Among the preferred compounds of the invention, there can be cited the compounds in which R$_2$ represents alkyl, alkenyl or alkynyl containing up to 6 carbon atoms, as well as their addition salts with pharmaceutically acceptable organic or mineral acids.

More particularly a subject of the invention is the compounds in which the radical —C(R$_1$)=NOR$_2$ is in position 3, as well as their addition salts with organic or mineral acids.

In particular a subject of the invention is the compounds in which n represents the number 1 and those in which n represents the number 2, as well as their addition salts with organic or mineral acids.

Among the preferred compounds of the invention, there can be cited quite specially the compounds in which R$_1$ represents hydrogen, as well as their addition salts with organic or mineral acids, the compounds in which, when n=2, R$_1$ and R$_2$ do not each represent a hydrogen atom, those in which R$_2$ represents linear, branched or cyclic alkyl containing up to 4 carbon atoms, as well as their addition salts with organic or mineral acids.

Quite specially a subject of the invention is 1-azabicyclo-[2,2,2]-octan-3-carboxaldehyde O-methyloxime, as well as its addition salts with organic or mineral acids, 1-azabicyclo-[2,2,2]-octan-3-yl ethanone O-methyloxime as well as its addition salts with organic or mineral acids and particularly its hydrochloride and 1-azabicyclo-[2,2,1]-heptan-3-carboxaldehyde as well as its addition salts with organic or mineral acids and particularly its sesqui oxalate.

The compounds of the invention have a very marked central cholinomimetic activity with a long duration of action.

Therefore a subject of the invention is the compounds of formula (I) and their addition salts with pharmaceutically acceptable organic or mineral acids, as medicaments useful in particular in the treatment of Alzheimer's disease, of senile dementia and also in the treatment of memory disorders of the aged.

A subject of the invention is more particularly, as medicaments, the compound of Example 1 and that of Example 4.

The usual posology is variable according to the affection in question, the patient being treated and the administration route; it can be between 1 mg and 100 mg/day, for example, between 1 and 15 mg/day in one or more doses for the product of Example 1, administered by oral route.

Also a subject of the present invention is the pharmaceutical compositions containing as the active principle at least one product of formula (I) or one of its salts with pharmaceutically acceptable organic or mineral acids. The pharmaceutical compositions of the invention can be solid or liquid and can be presented in the pharmaceutical forms currently used in human medicine, such as for example, plain or sugar-coated tablets, gelules, granules, suppositories, injectable preparations; they are prepared according to the usual methods.

The active principle or principles can be incorporated with the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivative, glycols, various wetting, dispersing and emulsifying agents, and preservatives.

Also a subject of the invention is a preparation process, characterized in that a compound of general formula (II):

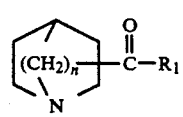

in which n and $R_1$ have the same meaning as above, is submitted to the action of a compound of general formula (III):

$$R_2ONH_2 \quad (III)$$

in which $R_2$ has the same meaning as above, so as to obtain the corresponding compound of formula (I), which, if desired, is salified.

In a preferred embodiment of the invention, the compounds of formula (III) are used in hydrochloride form.

The compounds of formula (II) in which $R_1$ represents hydrogen or alkyl are known in a general way; see in this regard *Zhur Obshchei Khim* 27, 72 (1957), *Helv. Chim. Acta.* 46, 2658 (1963), *Helv. Chim. Acta.* 55, 2439 (1972), *Heterocycles* 24, 971 (1986), *Helv. Chim. Acta.* 57, 2332 (1974).

The compounds of formula (II) in which $R_1$ represents hydrogen can be prepared according to the following reaction scheme:

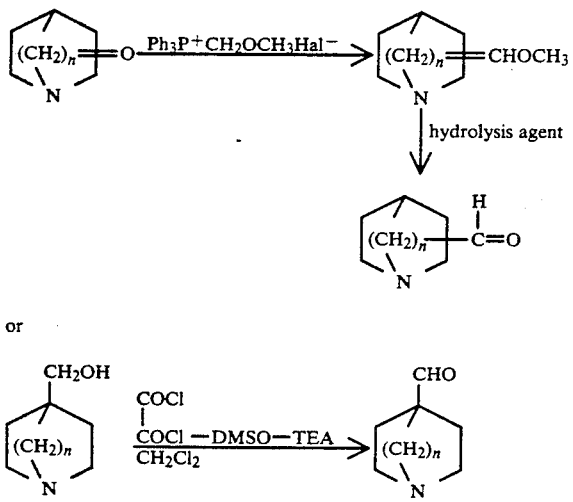

Hal preferably represents a chlorine or bromine atom. The hydrolysis agent is preferably perchloric acid.

The following examples illustrate the invention without however limiting it.

EXAMPLE 1

1-azabicyclo-[2,2,2]-octan-3-carboxaldehyde O-methyloxime 11 cm³ of a 70% aqueous solution of perchloric acid is added at ambient temperature to 4.6 g of 3-methoxy methylidene quinuclidine (Heterocycles 244, 4-971 (1986)) in solution in 46 cm³ of chloroform. After one hour of contact, 2.5 g of methoxylamine hydrochloride in 10 cm³ of water and 10 cm³ of methanol is added and the reaction medium is maintained in this way for one night, and is then concentrated, alkalized with 2N sodium hydroxide, extracted with ethyl acetate; the solvents are evaporated, and the residue is taken up in ethyl ether and filtered. The filtrate is distilled at 150° C. under 0.08 mbar and 3.2 g of expected product is obtained.

Analysis: $C_9H_{16}N_2O$ Calculated: C % 64.25, H % 9.59, N % 16.65. Found: C % 64.15, H % 9.54, N % 16.48.

EXAMPLE 2

1-azabicyclo-[2,2,2]-octan-3-carboxaldehyde O-ethyloxime 4.8 cm³ of a 70% aqueous solution of perchloric acid is added at ambient temperature to 2 g of 3-methoxy methylidene quinuclidine in solution in 20 cm³ of chloroform. After agitating for one hour, 1.4 g of O-ethylhydroxylamine hydrochloride in 2.5 cm³ of methanol and 2.5 cm³ of water are added, and the reaction medium is maintained in this way for one night. After concentrating, alkalizing with sodium hydroxide, extracting with ethyl acetate, and distilling at 135° C. under 0.05 mbar, 2.05 g of expected product is obtained.

Analysis: $C_{10}H_{18}N_2O$ Calculated: C % 65.90, H % 9.86, N % 15.37. Found: C % 65.89, H % 9.78, N % 15.23.

EXAMPLE 3

1-azabicyclo-[2,2,2]-octan-3-carboxaldehyde O-2-propynyloxime

The operation is carried out as in Example 1 using 1.75 g of 3-methoxy methylidene quinuclidine, 3.8 cm³ of perchloric acid and 1.22 g of O-2-propynylhydroxylamine hydrochloride (U.S. Pat. No. 3,398,180 (1968)). After the ethyl ether has been evaporated off, the residue is chromatographed on silica (eluant: chloroform-methanol 7-3) then distilled at 190° C. under 0.05 mbar and 1.35 g of expected product is obtained.

Analysis: $C_{11}H_{16}N_2O$ Calculated: C % 68.72, H % 8.39, N % 14.57. Found: C % 68.35, H % 8.40, N % 14.49.

EXAMPLE 4

(1-azabicyclo-[2,2,2]-octan-3-yl)-ethanone O-methyloxime hydrochloride 2.3 g of 3-acetyl quinuclidine hydrochloride (Helv. Chim. Acta (1963) 229, 2658) and 1.02 g of O-methylhydroxylamine hydrochloride are heated for 20 minutes to reflux in 30 cm³ of methanol. The solvent is evaporated and the residue is chromatographed on silica (eluant: chloroform-methanol 7-3). After crystallization from ethanol and from ether, 1.8 g of expected product is obtained. M.p.=186°-188° C.

Analysis: $C_{10}H_{18}N_2O$, HCl Calculated: C % 53.80 H % 8.80 N % 12.55. Found: C % 53.59 H % 8.94 N % 12.50.

EXAMPLE 5

(1-azabicyclo-[2,2,2]-octane-3-yl)-ethanone O-2-propynyloxime 1.8 g of 3-acetyl quinuclidine hydrochloride and 1.02 g of O-2-propynyl-hydroxylamine hydrochloride are heated for 20 minutes to reflux in 30 cm³ of methanol. After evaporating to dryness, the residue is chromatographed on silica (eluant: methanol-ethyl ether). An aqueous solution of potassium carbonate is added and extraction is carried out with ethyl acetate. The extracts are dried and distilled at 170° C. under 0.2 mbar. After cooling, 1.1 g of expected product is obtained. M.p.=56°-58° C.

Analysis: $C_{12}H_{18}N_2O$ Calculated: C % 69.87, H % 8.80, N % 13.58. Found: C % 69.26, H % 8.69, N % 13.43.

EXAMPLE 6

(1-azabicyclo-[2,2,2]-octan-3-yl)-ethanone
O-ethyloxime hydrochloride 1.9 g of 3-acetyl quinuclidine hydrochloride and 0.98 g of O-ethylhydroxylamine hydrochloride are heated for 20 minutes to reflux in 30 cm³ of methanol, followed by concentrating to dryness and purifying by chromatography on alumina (eluant: methylene chloride-methanol 9-1). The reaction medium is acidified using gaseous hydrochloric acid, then evaporated to dryness. After crystallizing from ethanol, filtering, and rinsing with ether, 1.3 g of expected product is recovered. M.p.=198°-200° C.

Analysis: $C_{11}H_{21}N_2O$ Calculated: C % 56.76, H % 9.10, N % 12.04. Found: C % 55.85, H % 9.02, N % 11.92.

EXAMPLE 7

(1-azabicyclo-[2,2,2]-octan-3-yl)-ethanone oxime and its hydrochloride 2.2 g of 3-acetyl quinuclidine hydrochloride and 0.81 g of hydroxylamine hydrochloride are heated to reflux in 30 cm³ of methanol. The product is concentrated to dryness and purified by chromatography on alumina (eluant: methylene chloride-methanol 9-1); 0.2 g of base is recovered, which is acidified with gaseous hydrochloric acid, and evaporated to dryness. After crystallizing from ethanol, filtering and rinsing with ether, 1.45 g of expected product is recovered in hydrochloride form.

Analysis carried out on the base: $C_9H_6N_2O$ Calculated: C % 64.25, H % 9.59, N % 16.65. Found: C % 64.33, H % 9.61, N % 16.64.

Melting point of the base=96°-98° C.

Operating as in Example 1 or Example 4 starting with appropriate compounds, the following products were prepared:

EXAMPLE 8

1-azabicyclo-[2,2,2]-octan-3-carboxaldehyde oxime hydrochloride

EXAMPLE 9

1-azabicyclo-[2,2,2]-octan-4-carboxaldehyde oxime

EXAMPLE 10

1-azabicyclo-[2,2,2]-octan-4-carboxaldehyde O-methyloxime hydrochloride 1.6 cm³ of dimethyl sulfoxyde are added dropwise to a mixture, cooled to −50°/−60° C., of 1.09 cm³ of oxalyl chloride and 30 cm³ of methylene chloride, after agitating for 15 minutes, 1.6 g of 4-hydroxy methylquinuclidine (Helv. Chim. Acta 57 (8) 2332 (1974)) in 50 cm³ of methylene chloride are added and the medium is agitated for 2 hours at −50°/−60° C. Then, 7.89 cm³ of triethylamine are added dropwise. The mixture is allowed to warm at room temperature, a solution of 0.95 g of O-methyl hydroxylamine hydrochloride in 30 cm³ of methanol is added and the reaction medium is maintained for 16 hours to room temperature. The solvents are evaporated to dryness, the residue is taken up with dichloromethane, alkalized with 2N sodium hydroxyde, after decantation the aqueous phase is then extracted with dichloromethane. The organic extracts are evaporated to dryness. The residue is dissolved in ethyl ether and the hydrochloride is obtained using gaseous hydrochloric acid. The solid is filtered off and crystallised in a mixture of ethanol ethyl ether. 0.91 g of expected product is obtained. M.P.=271°-271.5° C. (with decomposition).

Analysis: Calculated: C % 52.81, H % 8.37, N % 13.69. Found: C % 52.9, H % 8.36, N % 13.55.

EXAMPLE 11

1-azabicyclo-[2,2,2]-octan-4-carboxaldehyde O-propynyl oxime oxalate

Operating as in example 11 using O-propargyl hydroxylamine the expected product is obtained. M.P. 162° C. (with decomposition).

EXAMPLE 12

1-azabicyclo-[2,2,2]-octan-4-carboxaldehyde O-ethyl oxime

Operating as indicated above with the appropriated compounds, the expected product is obtained.

EXAMPLE 13

(1-azabicyclo-[2,2,2]-octan-4-yl)ethanone O-methyl oxime and its hydrochloride

A solution of 0.65 g of 4-acetylquinuclidine (Helv. Chim. Acta. 55 (7) 2439 (1972)) and 0.29 g of O-methyl hydroxylamine hydrochloride in 20 cm³ of methanol is agitated at ambiant temperature for 3 hours, then evaporated to dryness. The residue is taken up with 2N sodium hydroxyde, extracted with chloroform and the dried organic layer evaporated to dryness. The residue is taken up in ethanol, acidified with a 20% ethanolic hydrochloric acid solution, precipitated with ethyl ether. After filtration, the product is recrystallised in a mixture of ethanol-ethyl ether to obtain 0.7 g of expected product. M.P.>300° C.

Analysis: $C_{10}H_{18}N_2O$. HCl=218,728 Calculated: C % 54.91, H % 8.76, N % 12.81. Found: C % 54.87, H % 8.7, N % 12.53.

EXAMPLE 14

(1-azabicyclo-[2,2,2]-octan-4-yl) ethanone O-propynyl oxime

Operating as in example 13 with the appropriated compounds the expected product is obtained.

EXAMPLE 15

1-azabicyclo-[2,2,1]-heptan-3-carboxaldehyde O-methyl oxime and its sesqui oxalate Stage A: 1-azabicyclo-[2,2,1]-heptan-3-methoxy methylidene.

7 cm³ of a 1.6M solution of butyllythium is added, under reduced pressure, to a suspension of 3.86 g of (methoxymethyl) triphenyl phosphonium chloride in 20 cm³ of anhydrous ether. The mixture is agitated 15 minutes to ambiant temperature and then cooled to −35° C. and 1.25 g of 1-azabicyclo-[2,2,1]-heptan-3-one (J. Org. Chem. 1969, 34, 3674) in ether are added dropwise while maintaining the temperature at −35° C. The reaction medium is allowed to warm to ambiant temperature and maintained in this way for 16 hours. After filtration, the ether is evaporated off and the residue distilled under reduced pressure the product is recovered at ~100° C. under 15 mm Hg. 0.5 g of expected product are obtained.

Stage B: 1-azabicyclo-[2,2,1]-heptan-3-carboxaldehyde O-methyl oxime and its sesqui oxalate.

1 cm³ of 70% aqueous solution of perchloric acid is added in 10 minutes to a solution of 0.5 g of the product obtained in stage A above in 5 cm³ of chloroform. After 2 hours of agitation at ambiant temperature, 0.3 g of O-methyl hydroxylamine hydrochloride in solution in 1 cm³ of water and 3 cm³ of methanol are added. The mixture is agitated for 24 hours at ambiant temperature and then concentrated to dryness under reduced pressure. The residue is alkalized with 2N sodium hydroxyde, extracted with ethyl acetate and evaporated to dryness. The residue is taken up in ethyl acetate and treated with an equimolar solution of oxalic acid dihydrate in the same solvent. The oxalate is recrystallised in isopropanol to give 0.4 g of the expected product. M.P.=95°-97° C.

Analysis: $C_8H_{14}N_2O$, $(1.5\ C_2H_{H2}O_4)=C_{11}H_{17}N_2O_7$. P.M. 289,267 Calculated: C % 45.67, H % 5.92, N % 9.68. Found: C % 45.95, H % 5.98, N % 9.85.

The following product was also similarly prepared:

EXAMPLE 16

(1-azabicyclo-[2,2,1]-heptan-3-yl) ethanone O-methyl oxime.

EXAMPLE 17

Tablets were prepared corresponding to the following formula:

| Product of Example 1 | 50 mg |
|---|---|
| Excipient q.s. for a tablet completed at | 300 mg |

(Detail of excipient: lactose, talc, wheat starch, treated starch, rice starch, magnesium stearate).

EXAMPLE 18

Gelules were prepared corresponding to the following formula:

| Product of Example 1 | 60 mg |
|---|---|
| Excipient q.s. for a gelule completed at | 300 mg |

(Detail of excipient: aerosil, talc, magnesium stearate).

PHARMACOLOGICAL STUDY

Acute Toxicity

The test is carried out on male mice ($CD_1$ Charles Rivers) weighing 22 to 24 g, which have gone without food for 16 hours. The products are administered by oral route at a dose of 1000, 500, 250, 125, 62, 31 and 16 mg/kg. The mortality is noted during the 7 days following the treatment.

| Example | LD$_{50}$ mg/kg |
|---|---|
| 1 | 30 |
| 2 | 150 |
| 3 | 40 |
| 4 | 75 |
| Aceclidine, HCl | 250 |

Test on the Isolated Ileum of a Guinea-Pig

Pieces of ileum are removed from guinea-pigs which have been killed by decapitation. The isolated ileum is placed in 10 cm³ of Tyrode's solution at 37° C. and aerated by a mixture of oxygen (95%) and carbon dioxide (5%). The contractions due to the products are recorded using a sensor connected to a polygraph. The products being tested are added, in concentrations comprised between $1.10^{-3}M$ and $1.10^{-8} M/1$.

The products presenting a contracting effect are tested vis-à-vis atropine and hexamethonium to establish if the activity is of "muscarinic" or "nicotinic" type.

The agonist activity is expressed in $pD_2$ (negative logarithm of the dose which produces 50% of the maximum effect).

| Example | pD$_2$ |
|---|---|
| 1 | 7.30 |
| 4 | 7.02 |
| Aceclidine, HCl | 6.98 |

Diarrheic Activity

The test is carried out on male mice ($CD_1$ Charles Rivers) weighing 25 to 30 g, and without food for 6 hours. The product, dissolved at 5% in methocel, is administered by oral route, using an oesophagus probe.

Control animals receive only the excipient (20 ml/kg).

After treatment, the animals are put separately into cages, the bottom of which is covered with absorbent paper, and are observed for 30, 60, 120 and 180 minutes.

The absorbent sheets of paper are changed after each observation.

The consistency of the faeces is evaluated according to the Randall and Baruth method (Arch. Int. Pharmacodyn., 220, 94, 1976) in accordance with the following scale of values.

0: firm consistency,
1: slightly soft faeces with or without a damp ring,
2: slightly soft faeces with presence of a well-defined damp ring,
3: soft faeces with presence of a large damp ring,
4: faeces without consistency with presence of a very large damp ring.

For each product, the dose has been noted which cause diarrhoea in 50% of the animals according to the Miller and Tainter method (Proc. Soc. Exp. Biol. Med., 57, 261, 1944).

| Example | ED$_{50}$ mg/kg |
|---|---|
| 1 | 1.1 |
| 4 | 3 |
| Aceclidine, HCl | 4 |

Hypothermic Activity

The test is carried out on male mice ($CD_1$ Charles Rivers) weighing 25 to 30 g, and without food for 6 hours.

The body temperature is noted using a thermocouple placed in the rectum to about 1.5 cm and connected to an electrical temperature recorder.

The products are administered by oral or sub-cutaneous route and the temperatures are noted at 0 then 30 minutes, 1 hour, 2 hours and 2 hours 30 minutes after treatment.

The degree of hypothermia is evaluated as the difference between the treated animals and the control animals and the dose necessary to reduce the body temperature by 1° C. is determined.

| Example | Effective dose (−1° C.) in mg/kg | |
|---|---|---|
| | Oral route | Sub-cutaneous route |
| 1 | 0.19 | 0.18 |
| 4 | 0.33 | 0.33 |
| Aceclidine, HCl | 6.4 | 2.1 |

The duration of action of the products is determined by using doses capable of reducing the temperature by 1° to 1.2° C.

| Ex-ample | Dose mg/kg | Adminis-tration | treatment time in minutes | | | | |
|---|---|---|---|---|---|---|---|
| | | | 0 | 30 | 60 | 120 | 180 |
| 1 | 0.25 | oral | ±0 | −1.1** | −1.0** | ±0 | ±0 |
| | 0.25 | sub-cutaneous | ±0 | −1.2** | −1.1** | ±0 | ±0 |
| Aceclidine, HCl | 7.50 | oral | ±0 | −1.1** | −0.3* | ±0 | +0.1 |
| | 2.50 | sub-cutaneous | ±0 | −1.0** | −0.1 | +0.1 | +0.1 |

**Values significantly different from the controls (p < 0.01)
*Values significantly different from the controls (p < 0.05).

What is claimed is:

1. A compound of formula (I)

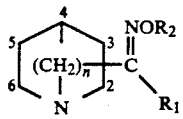

in which
n represents the number 1,
$R_1$ and $R_2$, identical or different represent hydrogen or an unsubstituted or substituted member of the group consisting of a linear, branched or cyclic alkyl, alkenyl, and alkynyl which contain up to 6 carbon atoms, in which the member, if substituted, is substituted by at least one of hydroxy, alkoxy containing up to 6 carbon atoms, benzyl, phenthyl, a COOalk$_1$ radical in which alk$_1$ represents alkyl containing up to 6 carbon atoms, and a —CON(alk$_2$)$_2$ radical in which alk$_2$ represents alkyl containing up to 6 carbon atoms, the radical —C($R_1$)=NOR$_2$ being in the 2, 3 or 4 position, in all their isomer forms, as well as its addition salts with pharmaceutically acceptable organic or mineral acids.

2. The compound of formula (I) as defined in claim 1, in which $R_2$ represents alkyl, alkenyl or alkynyl containing up to 6 carbon atoms, as well as its pharmaceutically acceptable salts with organic or mineral acids.

3. The compound of formula (I) as defined in claim 1 or 2, in which the radical —C($R_1$)=NOR$_2$ is in position 3, as well as its pharmaceutically acceptable addition salts with organic or mineral acids.

4. The compound of formula (I) as defined in claim 1, in which $R_1$ represents hydrogen, as well as its addition salts with pharmaceutically acceptable organic or mineral acids.

5. The compound of formula (I) as defined in claim 1, in which $R_1$ represents hydrogen, as well as its addition salts with pharmaceutically acceptable organic or mineral acids.

6. The compound of formula (I) as defined in claim 1 or 2, in which $R_1$ represents methyl, as well as its addition salts with pharmaceutically acceptable organic or mineral acids.

7. The compound of formula (I) as defined in claim 3, in which $R_1$ represents methyl, as well as its addition salts with pharmaceutically acceptable organic or mineral acids.

8. The compound of formula (I) as defined in claim 1 in which $R_1$ represents methyl, as well as its addition salts with pharmaceutically acceptable organic or mineral acids.

9. The compound of formula (I) as defined in claim 1 or 2, in which $R_2$ represents a linear, branched or cyclic alkyl containing up to 4 carbon atoms, as well as its pharmaceutically acceptable addition salts with organic or mineral acids.

10. The compound of formula (I) as defined in claim 3, in which $R_2$ represents a linear, branched or cyclic alkyl containing up to 4 carbon atoms, as well as its pharmaceutically acceptable addition salts with organic or mineral acids.

11. The compound of formula (I) as defined in claim 1, in which $R_2$ represents a linear, branched or cyclic alkyl containing up to 4 carbon atoms, as well as its pharmaceutically acceptable addition salts with organic or mineral acids.

12. The compound of formula (I) as defined in claim 6, in which $R_2$ represents a linear, branched or cyclic alkyl containing up to 4 carbon atoms, as well as its pharmaceutically acceptable addition salts with organic or mineral acids.

13. The compound of formula (I) as defined in claim 9, in which $R_2$ represents a linear, branched or cyclic alkyl containing up to 4 carbon atoms, as well as its pharmaceutically acceptable addition salts with organic or mineral acids.

14. The compound of formula (I) as defined in claim 1 or 2, in which $R_2$ represents methyl, as well as its pharmaceutically acceptable additional salts with organic or mineral acids.

15. The compound of formula (I) as defined in claim 3, in which $R_2$ represents methyl, as well as its pharmaceutically acceptable additional salts with organic or mineral acids.

16. The compound of formula (I) as defined in claim 1, in which $R_2$ represents methyl, as well as its pharmaceutically acceptable additional salts with organic or mineral acids.

17. A compound according to claim 1 selected from the group consisting of 1-azabicyclo-[2,2,1]-heptan-3-carboxaldehyde and addition salts thereof with pharmaceutically acceptable organic or mineral acids thereof.

18. A compound of claim 17 which is the sesqui oxalate of 1-azabicyclo-[2,2,1]-heptan-3-carboxaldehyde.

19. A therapeutic composition for the treatment of patients suffering from Alzheimer's disease, senile dementia, or memory disorders of the aged, comprising a cholinomimetic effective amount of a compound as defined in claim 1 or its acid addition salt with a pharmaceutically acceptable organic or mineral acid and a pharmaceutically acceptable carrier.

20. A method of treating patients suffering from Alzheimer's disease, senile dementia, or memory disorders of the aged, comprising administering to the patient a cholinomimetic effective amount of a compound as defined in claim 1 or its addition salts with a pharmaceutically acceptable organic or mineral acid.

* * * * *